United States Patent [19]

Siegel

[11] Patent Number: 5,876,925

[45] Date of Patent: *Mar. 2, 1999

[54] MAGNETICALLY ACTIVATED CELL SORTING FOR PRODUCTION OF PROTEINS

[75] Inventor: Donald L. Siegel, Hatboro, Pa.

[73] Assignee: The Trustees of the University of Pennsylvania, Philadelphia, Pa.

[21] Appl. No.: 884,045

[22] Filed: Jun. 27, 1997

Related U.S. Application Data

[60] Provisional application No. 60/028,550 Oct. 11, 1996.

[51] Int. Cl.$^6$ .............................. C12Q 1/68; C12Q 1/70; G01N 33/53; G01N 33/567
[52] U.S. Cl. .................................. 435/5; 435/6; 435/7.1; 435/7.21; 435/7.25
[58] Field of Search ........................... 435/5, 6, 7.1, 7.2, 435/7.21, 7.25, 69.1, 69.6, 91.1; 530/350, 380, 386, 387.1, 388.1, 388.15, 388.2, 388.7, 388.85; 536/23.1, 23.5, 23.53

[56] References Cited

U.S. PATENT DOCUMENTS

| | | | |
|---|---|---|---|
| 5,338,689 | 8/1994 | Yves et al. ............................... | 436/518 |
| 5,498,538 | 3/1996 | Kay et al. ............................... | 435/69.1 |
| 5,658,727 | 8/1997 | Barbas et al. ............................... | 435/6 |
| 5,663,143 | 9/1997 | Ley et al. ............................... | 514/12 |

FOREIGN PATENT DOCUMENTS

WO 95/31731  11/1995  WIPO .

OTHER PUBLICATIONS

Coia et al., 1996, J. Immunol. Methods, 192:13–23.
Hughes–Jones et al., 1994, British Journal of Haematology, 88:180–186.
Pereia et al., 1997, J. of Immunol. Methods, 203:11–24.
Siegel et al., 1997, J. of Immunol. Methds 206:73–85.
Winter et al., 1994, Annu. Rev. Immunol., 12:433–455.
DiaMed Ag Brochure, 1995, WorldWide pp. 1–6.
ID Microtyping System Brochure, 1995, Ortho Diagnostic System Inc., 14 pages.
Barbas, 1991, *Proc. Natl. Acad. Sci. USA* 88:7978–7982.
Barbas, 1995, "Synthetic human antibodies", *Nature Medicine* 1:837–839.
Barbas et al., 1991, Combinatorial Immunoglobulin Libraries On The Surface Of Phage (Phabs): Rapid Selection Of Antigen–Specific Fabs. *Methods: A Companion To Methods In Enzymology* 2:119–124.
Burton et al., 1994, "Human Antibodies from Combinatorial Libraries", *Adv. Immunol.* 57:191–280.
de Kruif et al., 1995, "Selection and Application of Human Single Chain Fv Antibody Fragments from a Semi–synthetic Phage Antibody Display Library with Designed CDR3 Regions", *J. Mol. Biol.*248:97–105.
Kang et al. 1991., Combinational Immunoglobulin Libraries On The Surface Of Phage (Phabs): Rapid Selection Of Antigen–Specific Fabs. *Methods: A Companion To Methods In Enzymology* 2:111–118.
Kretzschmar et al., 1995, Anal. Biochem. 224:413–419.
Lapierre et al., 1990, Transfusion 30:109–113.

Marks et al., 1991, "By–passign Immunization Human Antibodies from V–gene Libraries Displayed on Phage", *J. Mol. Biol.* 222:581–597.
Marks et al., 1993, "Human Antibody Fragments Specific for Human Blood group Antigens from a Phase Display Library", *Bio/Technology* 11:1145–1149.
Mollison et al., 1993, *Blood Transfusion in Clin. Medicine,* Oxford, Blackwell Scientific Publications—too voluminious to submit.
Roben et al., 1995, J. Immunol. 154:6437–6445.
Russell et al., 1993, "Retroviral vectors displaying functional antibody fragments", Nucl. Acids Res. 21:1081–1085.
Sambrook et al., 1989, Molecular Cloning: A Laboratory Manual, Cold Spring Harbor, NY—too voluminous to submit.
Siegel et al., 1994, Structural Analysis Of Red Cell Autoantibodies, Garratty (ed.) Immunobiology of Transfusion Medicine, Dekker, New York, NY, pp. 387–399.
Siegel, D., Submission entitled "A Plethora of Human Monoclonal Anti–Rh Antibodies Isolated Using Phage Display and Megnetically–Activated Cell Sorting", American Association of Blood Banks Annual Meeting, 1996, one page.
Silverman et al., 1995, *J. Clin. Invest.* 96:417–426.
Sternberg et al., 1995, "Display of peptides and proteins on the surface of bacteriophage λ", *Proc. Natl. Acad. Sci. USA* 92:1609–1613.
Tomlinson et al., 1996, *V Base Sequence Directory.* MRC Center for Protein Engineering, Cambridge, UK—too voluminous to submit.
Walker, ed. 1993, *Technical Manual, 11$^{th}$ Edition,* Bethesda: American Association of Blood Banks —too voluminous to submit.
Siegel et al. (1994) Expression and characterization of recombinant anti–Rh(D) antibodies on filamentous phage: a model system for isolating human red blood cell antibodies by repertoire cloning. 83:2334–2344, Apr. 1994.
De Kruif et al. (1995) Rapid selection of cell subpopulation–specific human monoclonal antibodies from a synthetic phage display library. Proc. Natl. Acad. Sci. USA 92:3938–3942, Apr. 1995.
Russo et al. (1992) Studies with biotinylated RBC: (1) use of flow cytometry to determine posttransfusion survival and (2) isolation using streptavidin conjugated magnetic beads. Adv. Exp. Med. Biol. 326:101–107, 1992.

*Primary Examiner*—George C. Elliott
*Assistant Examiner*—Robert Schwartzman
*Attorney, Agent, or Firm*—Panitch Schwarze Jacobs & Nadel, P.C.

[57] ABSTRACT

The invention includes methods of isolating DNA and a protein encoded thereby, the protein being capable of binding to an antigen-bearing moiety. The methods comprise generating a DNA library expressing the protein in a virus vector. A magnetic label is added to cells expressing the antigen-bearing moiety and the cells are incubated with virus expressing the protein in the presence of an excess of unlabeled cells which do not express the antigen-bearing moiety to form a mixture, wherein the virus binds to the magnetically labeled cells. Cells having virus bound thereon are isolated from the mixture and DNA encoding the protein and the protein are obtained therefrom.

24 Claims, 4 Drawing Sheets

Fig. 1

1. couple magnetic beads (·) to antigen-positive cells (⊘)

2. add excess antigen-negative cells (○)

3. add phage library containing specific ■ and non-specfic ⊂⊃ binders 4. incubate 5. load on column without magnetic field 6. place column in magnetic field and wash away antigen-negative cells and non-specific phage 7. flush antigen-positive cells and bound phage from column, elute bound phage, infect bacterial culture

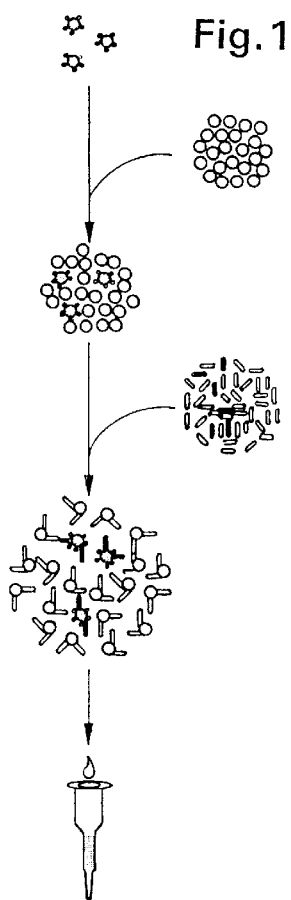
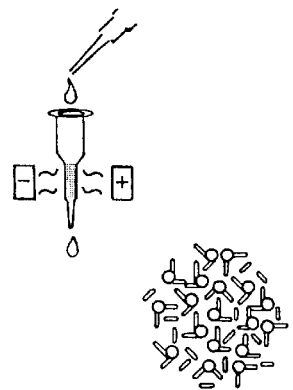

5,876,925

MAGNETICALLY ACTIVATED CELL SORTING FOR PRODUCTION OF PROTEINS

GOVERNMENT SUPPORT

This invention was supported in part by a grant from the U.S. Government (NIH Grant No. P50-HL54516) and the U.S. Government may therefore have certain rights in the invention.

CROSS REFERENCE TO RELATED APPLICATIONS

This application claims priority under 35 U.S.C. § 119(e) to U.S. Provisional Application No. 60/028,550, filed on Oct. 11, 1996.

1. Field of the Invention

The field of the invention is the generation of antibodies using recombinant DNA technology.

2. Background of the Invention

The ability to produce monoclonal antibodies has revolutionized diagnostic and therapeutic medicine. Monoclonal antibodies are typically produced by immortalization of antibody-producing mouse lymphocytes thus ensuring an endless supply of cells which produce mouse antibodies. However, for many human applications, it is desirable to produce human antibodies. For example, it is preferable that antibodies which are administered to humans for either diagnostic or therapeutic purposes are human antibodies since administration of human antibodies to a human circumvents potential immune reactions to the administered antibody, which reactions may negate the purpose for which the antibody was administered.

In addition, there exists certain situations where, for diagnostic purposes, it is essential that human antibodies be used because other animals are unable to make antibodies against the antigen to be detected in the diagnostic method. For example, in order to determine the Rh phenotype of human red blood cells (RBCs), human sera that contains anti-Rh antibody must be used since other animals cannot make an antibody capable of detecting the human Rh antigen.

The production of human antibodies in vitro by immortalizing human B lymphocytes using Epstein Barr virus (EBV)-mediated transformation or cell fusion has been fraught with technical difficulties due to the relatively low efficiency of both EBV-induced transformation and cell fusion when compared with the murine system. To overcome these problems, processes have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin (Ig) genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab Ig. Thus, in contrast to conventional monoclonal antibody synthesis, this procedure immortalizes DNA encoding human Ig rather than cells which express human Ig.

There are several difficulties associated with the generation of antibodies using bacteriophage. For example, many proteins cannot be purified in a non-denatured state, in that purification procedures necessarily involve solubilization of protein which may render some proteins permanently denatured with concomitant destruction of antigenic sites present thereon. Such proteins thus cannot be bound to a solid phase and therefore cannot be used to pan for phage bearing antibodies which bind to them. An example of such a protein is the human Rh antigen.

To solve the problem, a method was developed wherein intact RBCs were used as the panning antigen (Siegel et al., 1994, Blood 83:2334–2344). However, it was discovered that since phage are inherently "sticky" and RBCs express a multitude of antigens on the cell surface, a sufficient amount of phage which do not express the appropriate antibody on the surface also adhere to the RBCs, thus rendering the method impractical for isolation of phage which express antibody of desired specificity.

De Kruif et al. (1995, Proc. Natl. Acad. Sci. USA 92:3938–3942) disclose a method of isolating phage encoding antibodies, wherein antibody-expressing phage are incubated with a mixture of antigen-expressing cells and cells which do not express antigen. The antibody-expressing phage bind to the antigen-expressing cells. Following binding with phage, a fluorescently labeled antibody is added specifically to the antigen-expressing cells, which cells are removed from the mixture having antibody-expressing phage bound thereto. The isolation of fluorescently labeled cells is accomplished using the technique of fluorescently-activated cell sorting (FACS), an expensive and time-consuming procedure.

There remains a need for a method of isolating recombinant proteins, preferably antibodies, which is rapid and economical, and which will provide a vast array of protein-binding proteins useful for diagnostic and therapeutic applications in humans.

SUMMARY OF THE INVENTION

The invention relates to a method of isolating a DNA encoding a protein comprising generating a DNA library in a virus vector expressing the protein, wherein the protein is expressed on the surface of the virus vector and the protein is capable of binding to an antigen-bearing moiety, adding a magnetic label to cells expressing the antigen-bearing moiety, incubating virus expressing the protein with the magnetically labeled cells in the presence of an excess of unlabeled cells which do not express the antigen-bearing moiety to form a mixture, wherein the virus binds to the magnetically labeled cells, isolating virus bound cells from the mixture and obtaining DNA encoding the protein therefrom.

The invention also relates to a method of isolating a protein comprising generating a DNA library in a virus vector expressing the protein, wherein the protein is expressed on the surface of the virus vector and the protein is capable of binding to an antigen-bearing moiety, adding a magnetic label to cells expressing the antigen-bearing moiety, incubating virus expressing the protein with the magnetically labeled cells in the presence of an excess of unlabeled cells which do not express the antigen-bearing moiety to form a mixture, wherein the virus binds to the magnetically labeled cells, isolating virus bound cells from the mixture and isolating the protein therefrom.

In one aspect, the virus vector is a bacteriophage and in another aspect, the bacteriophage is M13.

In one aspect of the invention, the protein is selected from the group consisting of an antibody, a ligand and a hormone and in another aspect, the protein is an antibody which may be an anti-red blood cell surface antigen antibody, such as anti-Rh red blood cell antibody.

In yet another aspect of the invention, the antigen-bearing moiety is selected from the group consisting of a protein, a lipid, a carbohydrate, a nucleic acid and a complex of at least one of a protein, a lipid, a carbohydrate and a nucleic acid.

The antigen-bearing moiety may be a membrane bound protein which is selected from the group consisting of an antigen and a receptor. In another aspect, the membrane bound protein is an antigen, such as a red blood cell antigen, such as Rh antigen.

The invention also relates to a method of isolating a DNA encoding a protein capable of binding to an antigen-bearing moiety comprising generating a synthetic DNA library in a virus vector expressing the protein, adding a magnetic label to cells expressing the antigen-bearing moiety, incubating virus expressing the protein with the magnetically labeled cells in the presence of an excess of unlabeled cells which do not express the antigen-bearing moiety to form a mixture, wherein the virus binds to the magnetically labeled cells, isolating virus bound cells from the mixture and obtaining DNA encoding the protein therefrom.

The invention further relates to a method of isolating a protein capable of binding to an antigen-bearing moiety comprising generating a synthetic DNA library in a virus vector expressing the protein, adding a magnetic label to cells expressing the antigen-bearing moiety, incubating virus expressing the protein with the magnetically labeled cells in the presence of an excess of unlabeled cells which do not express the antigen-bearing moiety to form a mixture, wherein the virus binds to the magnetically labeled cells, isolating virus bound cells from the mixture and isolating the protein therefrom.

Methods are also provided wherein a protein capable of binding to an antigen-bearing moiety is isolated. The methods comprise expressing the protein from DNA encoding the protein, wherein the DNA is obtained by the methods described herein, and isolating the protein so expressed.

Also included in the invention is an isolated DNA encoding a protein obtained according to the methods described herein.

The invention also relates to a substantially pure preparation of a protein obtained according to the methods described herein.

BRIEF DESCRIPTION OF THE DRAWINGS

FIG. 1 is a diagram of a strategy for cell-surface Fab-phage panning using magnetically-activated cell sorting.

DETAILED DESCRIPTION

Figure 2:
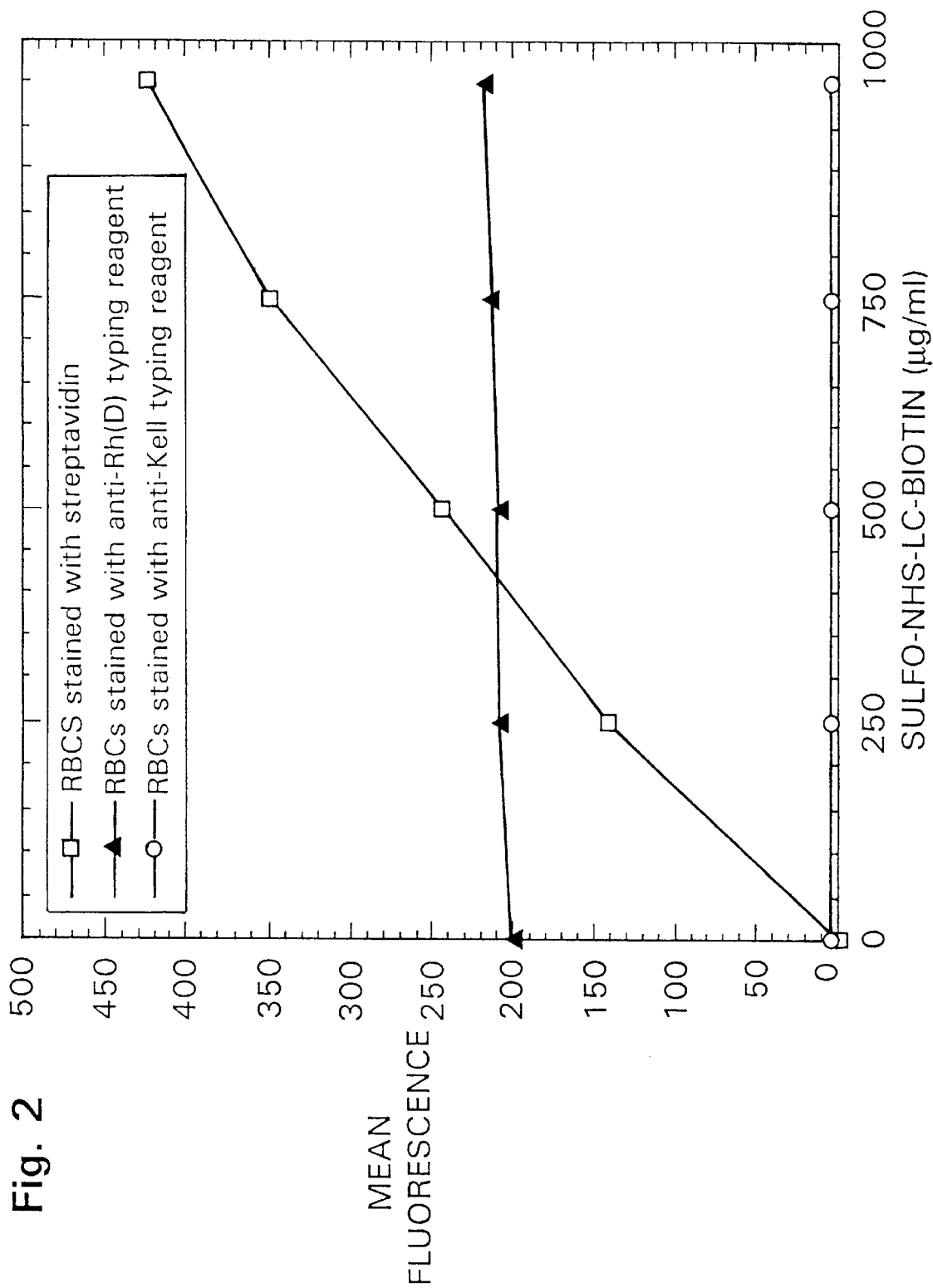
FIG. 2 is a graph depicting cell-surface biotinylation of human RBCs.

According to the present invention, there is provided a novel method of isolating DNA encoding a protein and the protein encoded thereby, wherein the protein is preferably an antibody, which protein is capable of specifically binding to an antigen-bearing moiety.

As exemplified herein but not limited thereto, the method comprises generating bacteriophage which encode human antibodies. Specifically in the present invention, anti-Rh(D) RBC Fab/phage antibodies encoded by an M13 filamentous phage library are obtained. The library is generated from antibody-producing cells obtained from a hyperimmunized donor by first obtaining cDNA derived from mRNA expressed in the antibody-producing cells. Ig encoding fragments of the cDNA are obtained using the polymerase chain reaction (PCR) and primers specific for such fragments of DNA. Ig-specific DNA so obtained is cloned into a bacteriophage. Bacteriophage encoding the Ig fragments are panned against a mixture of antigen-positive, biotinylated RBC-target cells pre-coated with streptavidin-conjugated magnetic microbeads and excess unlabeled RBCs. Bacteriophage which express antibodies on the phage surface, which antibodies are specific for the target cell antigen, bind to the labeled cells. These phage are separated from phage which are bound to unlabeled cells and from phage which are not bound to the cells using a magnetic column. Phage so separated encode and display antibody specific for antigens on the target cells.

To generate a phage antibody library, a cDNA library is first obtained from mRNA which is isolated from cells which express the desired protein to be expressed on the phage surface, e.g., the desired antibody. cDNA copies of the mRNA are produced using reverse transcriptase. cDNA which specifies Ig fragments are obtained by PCR and the resulting DNA is cloned into a suitable bacteriophage vector to generate a bacteriophage DNA library comprising DNA specifying Ig genes. The procedures for making a bacteriophage library comprising heterologous DNA are well known in the art and are described, for example, in Sambrook et al. (1989, *Molecular Cloning. A Laboratory Manual*, Cold Spring Harbor, N.Y.).

A bacteriophage library may also be obtained using cDNA rather than PCR-amplified Ig encoding fragments of cDNA. Generation of a CDNA library is useful for the isolation of proteins which are not antibodies, such as ligands and the like.

Bacteriophage which encode the desired protein, e.g., an antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell.

For panning of bacteriophage, i.e., selection of phage which express the desired antibody, cells which express the corresponding antigen are labeled with a detectable label such as biotin. Streptavidin-conjugated magnetic beads are then added to the cells. The cells are mixed with an excess of unlabeled cells which do not express the antigen. This cell mixture is then incubated with the phage library, wherein phage which express the antibody bind to cells expressing the antigen. The presence of the excess unlabeled cells in the mixture serves as a means of removing bacteriophage which do not express the antibody but which might otherwise bind to antigen-expressing cells non-specifically. The details of the experimental procedures for practicing the present invention are provided herein in the experimental detail section.

Antigen-expressing cells having antibody-expressing phage bound thereto are magnetically removed from the mixture. One example of magnetic removal involves pouring the mixture of magnetic and non-magnetic cells into a column in the selective presence or absence of a magnetic field surrounding the column. Alternatively, magnetic cells may be separated from non-magnetic cells in solution by simply holding a magnet against the side of a test tube and attracting the cells to the inner wall and then carefully removing the non-magnetic cells from the solution.

Thus, the method of the invention involves a procedure for enriching a population of recombinant phage for those expressing specific phage-displayed ligands derived from natural or synthetic phage DNA libraries by simultaneously performing negative and positive selection against a mixture of magnetically-labeled receptor-positive particles (i.e., cells) and unlabeled receptor-negative particles.

The terms "bacteriophage" and "phage" are used interchangeably herein and refer to viruses which infect bacteria. By the use of the terms "bacteriophage library" or "phage library" as used herein, is meant a population of bacterial viruses comprising heterologous DNA, i.e., DNA which is not naturally encoded by the bacterial virus.

The term "virus vector" includes a virus into which heterologous DNA has been inserted. The virus vector may be a bacteriophage or may be a eukaryotic virus.

By the term "target cell" as used herein, is meant a cell which expresses an antigen against which the desired antibody is sought.

By the term "panning" or "panned" as used herein, is meant the process of selecting phage which encode the desired antibody.

By the term "Fab/phage" as used herein, is meant a phage particle which expresses the Fab portion of an antibody.

By the term "scFv/phage" are used herein, is meant a phage particle which expresses the Fv portion of an antibody as a single chain.

By "excess unlabeled cells" is meant an amount of unlabeled cells which exceeds the number of labeled cells. Preferably, the ratio of labeled cells to unlabeled cells is about 1:2. More preferably, the ratio of labeled cells to unlabeled cells is greater than about 1:4. Even more preferably, the ratio of labeled cells to unlabeled cells is greater than about 1:10.

While the method of the invention as exemplified herein describes the generation of phage which encode the Fab portion of an antibody molecule, the method should not be construed to be limited solely to the generation of phage encoding Fab antibodies. Rather, phage which encode single chain antibodies (scFV/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFV DNA may be generated following the procedures described in Marks et al., 1991, *J. Mol. Biol.* 222:581–597. Panning of phage so generated for the isolation of a desired antibody is conducted as described herein for phage libraries comprising Fab DNA.

The invention should also be construed to include synthetic phage display libraries in which the heavy and light chain variable regions may be synthesized such that they include nearly all possible specificities. Therefore, antibody-displaying libraries can be "natural" or "synthetic" (Barbas, 1995, *Nature Medicine* 1:837–839; de Kruif et al. 1995, *J. Mol Biol.*248:97–105). Antibody-displaying libraries comprising "natural" antibodies are generated as described in the experimental example section. Antibody-displaying libraries comprising "synthetic" antibodies are generated following the procedure described in Barbas (1995, supra) and the references cited therein.

The method of the invention should be further construed to include generation of phage display libraries comprising phage other than M13 as exemplified herein. Other bacteriophage, such as lambda phage, may also be useful in the method of the invention. Lambda phage display libraries have been generated which display peptides encoded by heterologous DNA on their surface (Sternberg et al., 1995, *Proc. Natl. Acad. Sci. USA* 92:1609–1613). Moreover, it is contemplated that the method of the invention may be extended to include viruses other than bacteriophage, such as eukaryotic viruses. In fact, eukaryotic viruses may be generated which encode genes suitable for delivery to a mammal and which encode and display an antibody capable of targeting a specific cell type or tissue into which the gene is to be delivered. For example, retroviral vectors have been generated which display functional antibody fragments (Russell et al., 1993, *Nucl. Acids Res.* 21:1081–1085).

The red blood cell antibodies to which antibodies may be generated include, but are not limited to, Rh antigens, including Rh(D), Rh(C), Rh(c), Rh(E), Rh(e), and other non-Rh antigens, including red blood cell antigens in the Kell, Duffy, Lutheran and Kidd blood groups.

Thus, the method of the invention is not limited solely to the isolation of DNA encoding anti-Rh(D) antibodies, but rather may be used for the isolation of DNA encoding antibodies directed against any RBC antigen or other cell antigen, such as, but not limited to, tumor-specific antigen, bacterial antigens, and the like. The method of the invention is also useful for typing platelets by generating phage antibodies specific for a number of clinically important platelet antigens, notably, $Pl^{A1}/Pl^{A2}$, $Bak^a/Bak^b$, $Pen^A/Pen^B$, and the like.

The invention is further useful for typing donor white blood cells for HLA antigens for the purposes of matching donors and recipients for potential transplant matching in the case of both solid (for example, kidney, heart, liver, lung) and non-solid (for example, bone marrow) organ or tissue transplanting.

To detect binding of phage expressing antibody directed against one of these non-red blood cell antigens, the non-red blood cells may be agglutinated or trapped following the procedures described herein for agglutination or trapping of red blood cells. Prior to agglutination or trapping, the cells may be rendered "visible" by staining or other labeling technique in order that agglutination or trapping is apparent to the naked eye or scanner.

The method of the invention is most useful for the generation of a protein which binds to an antigen-bearing moiety, where the antigen-bearing moiety is not easily purified in soluble form. Thus, the antigen-bearing moiety includes antigens which are associated with other structures, usually membranes in the cell such as cell membranes or cell organelle membranes.

In accordance with the present invention, the antigen-bearing moiety may be a protein, a lipid, a carbohydrate or a nucleic acid, or it may be a complex of at least two of a protein, a lipid, a carbohydrate and a nucleic acid, it being appreciated that many antigen-bearing moieties in cells are not comprised of one of these components alone. Preferably, the antigen-bearing moiety is a membrane bound protein, such as an antigen or a receptor protein. However, when the antigen-bearing moiety is a carbohydrate, it may be a carbohydrate expressed on a glycolipid, for example, a P blood group antigen or other antigen.

By the term "antigen-bearing moiety" as used herein, is meant a molecule to which an antibody binds.

The method of the invention is also useful for the generation of autoimmune antibodies such as those involved in autoimmune hemolytic anemia (AIHA) (Siegel et al., 1994, *Structural analysis of red cell autoantibodies*, Garratty (ed) *Immunobiology of Transfusion Medicine*, Dekker, New York, N.Y.). Autoimmune antibodies that are directed against cell antigens which are cell surface membrane associated or cell organelle membrane associated may be isolated using the technology described herein. Autoimmune diseases and their associated antigens to which antibodies may be isolated include, but are not limited to the following: Myasthenia gravis (acetylcholine receptor; neurons), chronic inflammatory demyelinating polyneuropathy (myelin; neurons), autoimmune thyroid disease (thyroid stimulating hormone receptor; thyroid cells), primary biliary cirrhosis (mitochondrial autoantigens; liver mitochondria), idiopathic thrombocytopenic purpura (platelet membrane integrins; platelets), pemphigus vulgaris (epidermal antigens; epidermis), and Goodpasture's syndrome (basement membrane antigens; kidney or lung cells).

In fact, the method of the invention is useful for the isolation of DNA clones encoding any antibody directed against an antigen expressed on a cell, which cell can be labeled with a magnetic label and which cell can be obtained in sufficient quantities in an unlabeled form so as to provide an excess of unlabeled cells as required in the assay.

Further, the method of the invention is not limited to the isolation of DNA encoding antibodies but rather may also be used for the isolation of DNA encoding other peptides or proteins having specificity for cell proteins, such as, for example, but not limited to, ligands which bind cell receptor proteins, peptide hormones, and the like.

The invention should also not be construed as being limited to the use of biotin as the cell-labeling agent. Other labels may be used provided their addition to a cell does not disturb the structural integrity of any surface proteins expressed thereon and provided such labels permit the addition of a paramagnetic microbead or other magnetic substance thereto. Other such labels include, but are not limited to, cell surface proteins or carbohydrates which can be directly derivitized with magnetic beads that possess activated amine, carboxyl, or thiol groups. In addition, dyes such as fluorescein or rhodamine may also be covalently attached to cells in a manner similar to biotin and magnetic beads coated with anti-dye antibodies may be attached thereto.

The invention includes proteins and DNA encoding the same which are generated using the methods described herein. To isolate DNA encoding an antibody, for example, DNA is extracted from antibody expressing phage obtained according to the methods of the invention. Such extraction techniques are well known in the art and are described, for example, in Sambrook et al. (supra).

An "isolated DNA", as used herein, refers to a DNA sequence, segment, or fragment which has been purified from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to DNA which has been substantially purified from other components which naturally accompany the DNA, e.g., RNA or DNA or proteins which naturally accompany it in the cell.

The invention should also be construed to include DNAs which are substantially homologous to the DNA isolated according to the method of the invention. Preferably, DNA which is substantially homologous is about 50% homologous, more preferably about 70% homologous, even more preferably about 80% homologous and most preferably about 90% homologous to DNA obtained using the method of the invention.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGCG 5' share 50% homology.

To obtain a substantially pure preparation of a protein comprising, for example, an antibody, generated using the methods of the invention, the protein may be extracted from the surface of the phage on which it is expressed. The procedures for such extraction are well known to those in the art of protein purification. Alternatively, a substantially pure preparation of a protein comprising, for example, an antibody, may be obtained by cloning an isolated DNA encoding the antibody into an expression vector and expressing the protein therefrom. Protein so expressed may be obtained using ordinary protein purification procedures well known in the art.

As used herein, the term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g. a protein, is also substantially purified when it is essentially free of naturally associated components or when it is separated from the native contaminants which accompany it in its natural state.

The present invention also provides for analogs of proteins or peptides obtained according to the methods of the invention. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In addition to substantially full length polypeptides, the present invention provides for active fragments of the polypeptides. A specific polypeptide is considered to be active if it binds to an antigen-bearing moiety, for example, if a fragment of an antibody binds to its corresponding antigen in the same manner as the full length protein.

As used herein, the term "fragment," as applied to a polypeptide, will ordinarily be at least about fifty contiguous amino acids, typically at least about one hundred contiguous amino acids, more typically at least about two hundred continuous amino acids and usually at least about three hundred contiguous amino acids in length.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The experimental examples described herein provide procedures and results for the isolation and production of anti-Rh(D) red blood cell antibodies using Fab/phage display.

A method is described in FIG. 1 for the isolation of filamentous phage-displayed human monoclonal antibodies specific for unpurifiable cell surface expressed molecules. To optimize the capture of antigen-specific phage and minimize the binding of irrelevant phage antibodies, a simultaneous positive and negative selection strategy was employed. Cells bearing the antigen of interest are pre-coated with magnetic beads and are diluted into an excess of unmodified antigen-negative cells. Following incubation of the cell admixture with a Fab/phage library, the antigen positive cell population is retrieved using magnetically-activated cell sorting, and antigen-specific Fab/phage are eluted and propagated in bacterial culture. When this protocol was used with magnetically-labeled (Rh(D)-positive and excess unlabeled Rh(D)-negative human red blood cells and a Fab/phage library constructed from human peripheral blood lymphocytes, dozens of unique, clinically useful $_{\gamma 1}\kappa$ and $_{\gamma 1}\lambda$ anti-Rh(D) antibodies were isolated from a single alloimmunized individual.

The cell-surface selection method of the present invention is readily adaptable for use in other systems, such as for the identification of putative tumor-specific antigens, and provides a rapid (less than one month), high yield approach for isolating self-replicative antibody reagents directed at novel or conformationally-dependent cell-surface epitopes.

Creation of Fab/Phage Display Libraries

Separate $_{\gamma 1}\kappa$ and $_{\gamma 1}\lambda$ phage libraries were constructed from $2 \times 10^7$ mononuclear cells derived from the peripheral blood from an Rh(D)-negative individual previously hyperimmunized with Rh(D)-positive red blood cells (RBCs). The phagemid vector pComb3 (Barbas, 1991, Proc. Natl. Acad. Sci. USA 88:7978–7982) was used to create the libraries utilizing previously published methods (Barbas et al., 1991, Combinatorial immunoglobulin libraries on the surface of phage (Phabs): Rapid selection of antigen-specific Fabs. Methods: A Companion to Methods in Enzymology 2:119–124; Siegel et al., 1994, Blood 83:2334–2344).

Briefly, cDNA was prepared from the mRNA of the donor cells and heavy chain and light chain immunoglobulin (Ig) cDNA segments were amplified using the polymerase chain reaction (PCR) and the battery of human Ig primers described by Kang et al. (1991, "Combinatorial Immunoglobulin Libraries on the Surface of Phage (Phabs): Rapid Selection of Antigen-Specific Fabs. Methods: A Companion to Methods" in Enzymology 2:111–118) supplemented by those of Silverman et al. (1995, J. Clin. Invest. 96:417–426). The heavy and light chain PCR products were cloned into pComb3 and electroporated into E. coli. Upon co-infection with VCSM13 helper phage (Stratagene, La Jolla, Calif.), Ig DNA was packaged into filamentous phage particles which express human Fab molecules fused to the gene III bacteriophage coat protein.

Panning Fab Phage Display Libraries for Anti-Rh (D) Clones

Rh(D)-positive RBCs were cell-surfaced biotinylated by incubating cells at a hematocrit of 10% with 500 $\mu$g/ml sulfo-NHS-LC-biotin (Pierce Chemical, Rockford, Ill.) for 40 minutes at room temperature (RT). Following 5 washes with phosphate-buffered saline (PBS), $8 \times 10^6$ biotinylated Rh(D)-positive RBCs were incubated with 10 $\mu$l of streptavidin-coated paramagnetic microbeads (MACS Streptavidin Microbeads, Mitenyi Biotec, Sunnyvale, Calif.) for 1 hour at RT in a total volume of 100 $\mu$l PBS. Unreacted beads were removed by washing and then the magnetic bead-coated, Rh(D)-positive RBCs were mixed with a 10-fold excess ($8 \times 10^7$) of the Rh(D)-negative (unmodified) RBCs and $\sim 3 \times 10^{11}$ colony-forming units (cfu) of either the $_{\gamma 1}\kappa$ and $_{\gamma 1}\lambda$ Fab/phage libraries (prepared as described above) in a final volume of 40 $\mu$l PBS containing 2% non-fat dry milk (MPBS, Carnation, Nestle Food Products, Glendale, Calif.).

Following a 2 hour incubation at 37° C., the RBC/phage suspension was loaded at a flow rate of 10 µl/minute onto a MiniMACS magnetic type MS column (Mitenyi Biotec, Sunnyvale, Calif.) that was pre-equilibrated with 2% MPBS. This loading step was performed without a magnetic field around the column so as to prevent magnetic bead-coated RBCs from instantly adhering to the very top of the column, clogging it, and causing the trapping of Rh(D)negative unbiotinylated RBCs. Loading the RBC/phage incubation mixture in the absence of a magnetic field causes the antigen-negative and antigen-positive RBCs to distribute evenly throughout the column without running off since the excluded volume of the column is slightly greater than 40 µl. Once loaded, the column was placed in a magnetic field (MiniMACS magnetic separation unit, Mitenyi Biotec, Sunnyvale, Calif.) for 2 minutes to allow the Rh(D)-positive RBCs to adhere, and a series of 500 µl washes were performed with ice-cold MPBS followed by a final wash with PBS. A total of 3 washes were performed for the first 2 rounds of panning and a total of 6 washes were performed for all subsequent pannings. For each panning, the first wash was carried out at a flow rate of 10 µl/minute during which time the bulk of Rh(D)-negative RBCs washed off the column. All subsequent washes were performed at 200 µl/minute. Following the last wash, the column was removed from the magnetic field and the bead-coated/phage-coated Rh(D)-positive RBCs were flushed off the column with 500 µl PBS using the plunger from a 5 cc syringe (Becton-Dickinson, Franklin Lakes, N.J.).

The RBCs were immediately centrifuged for 5 seconds at 13,000×g and were then resuspended in 200 µl of 76 mM citrate, pH 2.4, to denature the Rh(D) antigen and elute bound phage. Following a 10 minute incubation period at RT with intermittent vortexing, the phage eluate and cellular debris were neutralized with 18 µl 2M Tris base and were added to 10 ml of O.D.=1.0 XL1-Blue strain of E. coli (Stratagene, La Jolla, Calif.) grown in super broth (SB) (Barbas et al, 1991, supra) supplemented with 10 µg/ml tetracycline. After incubation for 15 minutes at RT, during which time the phage library enriched for Rh(D) binders was allowed to infect the bacterial culture, 10 ml of pre-warmed, 37° C. SB containing 40 µg/ml carbenicillin/10 µg/ml tetracycline was added to give final antibiotic concentrations of 20 µg/ml and 10 µg/ml, respectively. A small aliquot of culture (~100 µl) was immediately removed and titered on LB/carbenicillin plates to determine the number of phage contained in the total eluate. The balance of the culture was shaken at 37° C. for 1 hour at 300 RPM. Additional antibiotics, additional SB, and VCSM13 helper phage were subsequently added and the culture was grown overnight at 30° C. as described (Siegel et al., 1994, supra).

Phagemid particles were purified from the culture supernatant by polyethylene glycol 8000 (PEG) precipitation (Barbas et al., 1991, supra), resuspended in 1% bovine serum albumin (BSA)/PBS, and dialyzed overnight to remove residual PEG that may lyse RBCs during subsequent rounds of panning. Thus, the resultant phage preparation serves as the input for the next round of panning. The $_{\gamma 1}\kappa$ and $_{\gamma 1}\lambda$ phage libraries were panned separately to prevent any bias in light chain isotype replication possibly introduced by bacterial amplification.

Screening Polyclonal Fab/Phage Libraries and Individual Phage Colonies for Anti-Rh(D) Reactivity The specificity of Fab/phage for the Rh(D) antigen was assessed using anti-M13 antibody as a bridging antibody to induce agglutination between RBCs that have bound anti-Rh(D) Fab/phage. One hundred µl aliquots of polyclonal Fab/phage from rounds of panning, or monoclonal Fab/phage derived from individual Fab/phage eluate clones, were incubated with 50 µl of a 3% suspension of RBCs of defined phenotype (i.e., Rh(D)-negative or -positive).

Following 1 hour incubation at 37° C., the RBCS were washed 3 times with 2 ml cold PBS to remove unbound Fab/phage. The resultant RBC pellets were resuspended in 100 µl of a 10 µg/ml solution of sheep anti-M13 antibody (5-Prime 3-Prime, Boulder, Colo.) and transferred to the round-bottomed wells of a 96-well microtiter plate. Plates were left undisturbed (~2 hours) and were then read. Wells having a negative reaction exhibit sharp ~2 mm diameter RBC spots whereas in wells having positive reactions, i.e., agglutination, the RBCs in agglutinated wells form a thin carpet coating the entire floor of the well.

For hemagglutination assays utilizing minicolumn gel cards (ID-Micro-Typing System, Ortho Diagnostics, Raritan, N.J.) (Lapierre et al., 1990, Transfusion 30:109–113), 25 µl of Fab/phage clones were mixed with 50 µl aliquots of RBCs (0.8% suspensions in Micro Typing System buffer, Ortho Diagnostics). The mixtures were placed in the reservoirs above the minicolumns which contain dextran-acrylamide beads previously suspended in 100 µl/ml anti-M13 antibody. After incubation at 37° C., the gel cards were centrifuged at 70×g for 10 minutes and were read.

Miscellaneous Methods

Preparation of fluorescently-labeled RBCs for flow cytometry was performed as described herein and samples were analyzed using a FACScan microfluorimeter equipped with Lysis II (Ver 1.1) software (Becton-Dickinson, Mountain View, Calif.). Plasmid DNA was prepared from bacterial clones (Qiawell Plus, Qiagen, Chatsworth, Calif.). Double-stranded DNA was sequenced using light chain or heavy chain Ig constant region reverse primers or unique pComb3 vector primers that anneal 5-prime to the respective Ig chain (Barbas et al., 1991, supra; Roben et al., 1995, J. Immunol. 154:6437–6445) and automated fluorescence sequencing (Applied Biosystems, Foster City, Calif.). Sequences were analyzed using MacVector Version 5.0 sequencing software (Oxford Molecular Group, Oxford, UK) and the Tomlinson database of Ig germline genes (Tomlinson et al., 1996, V Base Sequence Directory. MRC Center for Protein Engineering, Cambridge, UK).

Experimental Design for Cell Incubation and Separation Protocols

The experimental conditions described above for panning Fab/phage libraries for anti-RBC-reactive phage were determined after performing a series of initial studies aimed at optimizing the cell separation process and ultimate yield of antigen-specific Fab/phage. The main parameters investigated included:

Biotinylation Conditions were sought that would biotinylate the RBC surface in a manner such that a sufficient number of streptavidin-coated magnetic beads would bind to the cells causing the RBCs to be retained by a magnetic column. In this case, over-biotinylation that might destroy the antigenicity of the Rh(D) antigen or might make the cells non-specifically absorb antibody is to be avoided. To address this issue, Rh(D)-positive/Kell-negative RBCs (Kell being a RBC antigen; (Walker, ed. 1993, *Technical Manual*, 11$^{th}$ Edition, Bethesda: American Association of Blood Banks) were incubated with a range of sulfo-NHS-LC-biotin concentrations and the degree of biotinylation was assessed by flow cytometry utilizing fluorescein-conjugated streptavidin.

To assess the degree of cell-surface biotinylation, 5 μl aliquots of 3% suspensions of Rh(D)-positive/Kell-negative RBCs biotinylated at varying biotin reagent concentrations were incubated with 200 μl of a 1/100 dilution of FITC-streptavidin (Jackson ImmunoResearch, Bar Harbor, Me.) for 30 min at 4° C. (FIG. 2). The mixture was washed with phosphate buffered saline (PBS) and analyzed by flow microfluorimetry (-□-). Aliquots of cells were also analyzed for retention of Rh(D)-antigenicity (-Δ-) (i.e., specific staining) or for lack of non-specific staining (-○-) by incubating the cells with 100 μl of either anti-Rh(D) or anti-Kell typing sera, respectively, washing the cells and then staining them with a 1/100 dilution of FITC-goat anti-human IgG (Jackson ImmunoResearch).

A linear, non-saturating response was observed (FIG. 2). Retention of Rh(D) antigenicity was assessed using anti-Rh(D) typing serum and was found to be unaffected by the derivatization of cell-surface proteins with biotin at all biotin concentrations tested (FIG. 2). Furthermore, the Kell-negative RBCs did not non-specifically adsorb anti-Kell antibodies.

Each biotinylated RBC sample was then incubated with an excess of streptavidin-coated magnetic microbeads and applied to a magnetic separation column. It was determined that as many as $10^8$ RBCs could be retained by the column for RBC samples biotinylated with greater than or equal to 500 μg/ml biotin reagent. Since the actual RBC/phage panning experiments were designed to use only ~$10^7$ Rh(D)-positive cells (see below), RBC biotinylation at 500 μg/ml was determined to be sufficient.

Concentration of Rh(D)-positive and Rh(D)-negative RBCs in incubation mixture

Figure 3A:
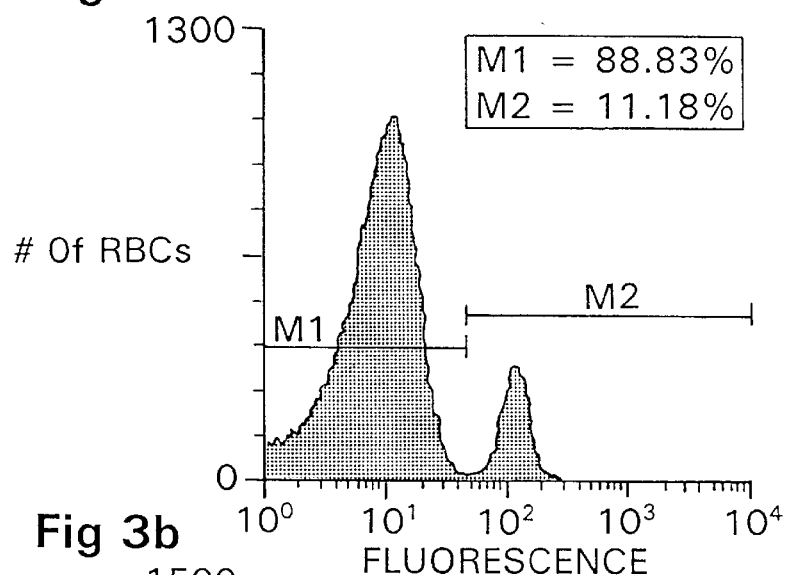
FIGS. 3A–3C are a series of graphs which validate the antigen-positive, antigen-negative cell separation procedure of the invention.
Figure 3B:
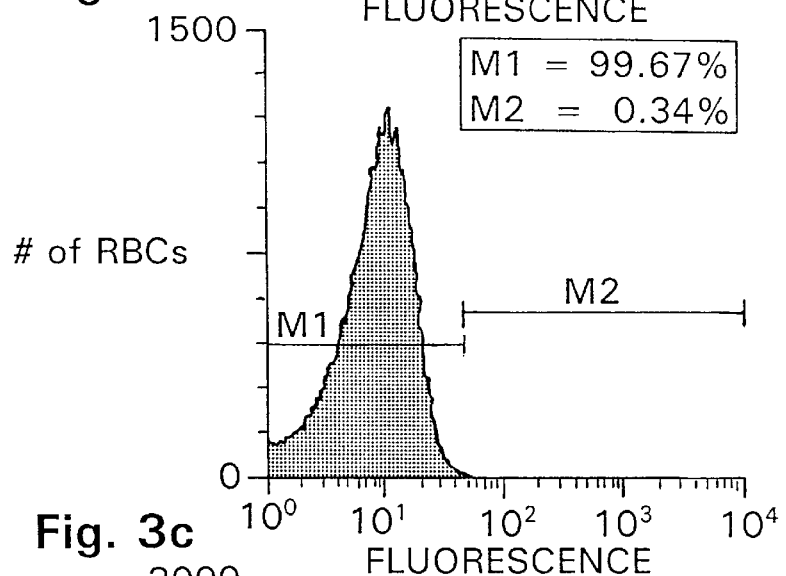
Figure 3C:
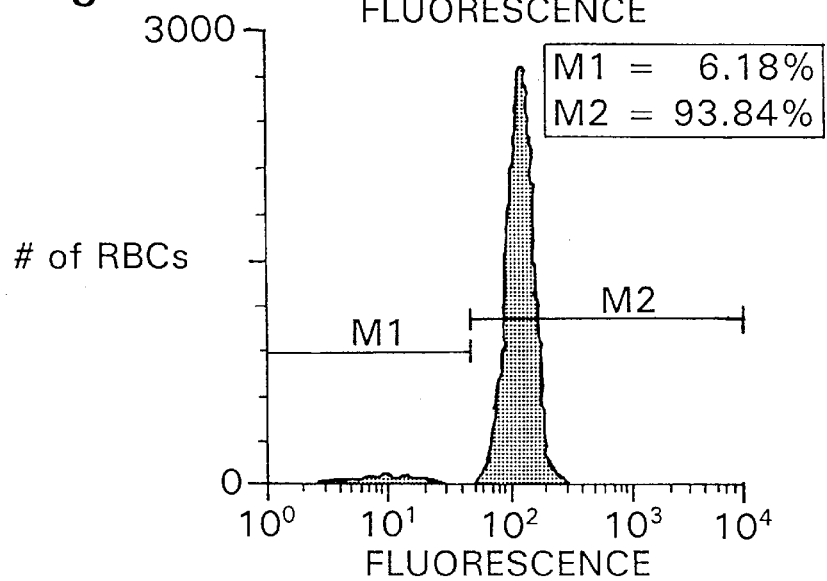

Prior to performing Fab/phage panning experiments, the ability of the magnetically-activated cell separation technique to separate Rh(D)-positive and Rh(D)-negative cells was assessed using anti-Rh(D) typing serum and flow cytometry (FIG. 3). Streptavidin-microbead coated, biotinylated Rh(D)-positive RBCs ($8 \times 10^6$ cells) were mixed with a 10-fold excess of Rh(D)-negative uncoated RBCs ($8 \times 10^7$ cells) in a 40 μl volume of PBS containing 2% non-fat dry milk (MPBS) and the mixture was applied to a MiniMACS column. The column was washed and the bound cells were eluted as described herein. Aliquots of RBCs contained in the original admixture (panel a), the column wash (panel b), and the column eluate (panel c) were stained with anti-Rh(D) typing serum and FITC-goat anti-human IgG as described in FIG. 2. The flow cytograms show that although ~90% of the cells in the column load were Rh(D)-negative (panel a), nearly all of them washed off of the column (panel b), yielding a column eluate that was almost entirely Rh(D)-positive cells (panel c). Since only ~6% of the final eluate comprise Rh(D)-negative cells (panel c), and Rh(D)-negative cells were initially present in a 10-fold excess to Rh(D)-positive cells, only ~0.6% of the initial antigen-negative immunosorbant cells contaminated the final antigen-positive preparation. This efficiency of the cell separation was deemed adequate for subsequent panning experiments with Fab/phage.

In the above-described experiment, to avoid clogging the magnetic separation column, it was necessary to load the column in the absence of a magnetic field. This necessitated a reaction volume of less than or equal to 40 μl so that none of the material would run off the column. On theoretical grounds (Kretzschmar et al., 1995, Anal. Biochem. 224:413–419), one can calculate the appropriate concentration of cells required in a 40 μl volume to capture greater than 50% of Fab/phage specific for a given cell surface antigen. Such a calculation is a function of the number of antigen sites per cell and the dissociation constant ($K_D$) of the bound Fab/phage. Using a value of ~100,000 Rh(D) antigen sites per RBC (phenotype "-D-/-D-") (Mollison et al., 1993, *Blood Transfusion in Clinical Medicine*, Oxford, Blackwell Scientific Publications) and the desired Fab/phage affinity in the $K_D = 10^{-8}$ to $10^{-9}$M range, then $8 \times 10^6$ Rh(D)-positive RBCs in a 40 μl reaction volume would be required. Given this number of Rh(D)-positive cells, a 10-fold excess of Rh(D)-negative RBCs was found to be the maximum amount of antigen-negative cells that could be effectively separated from antigen-positive RBCs by the magnetic column (FIG. 3).

Construction and Panning of Fab/Phage Libraries $_{γ1}κ$ and $_{γ1}λ$ phage libraries were prepared as described herein and were found to contain $7 \times 10^7$ and $3 \times 10^8$ independent transformants, respectively. Table 1 tabulates the panning results for the libraries.

Figure 4:
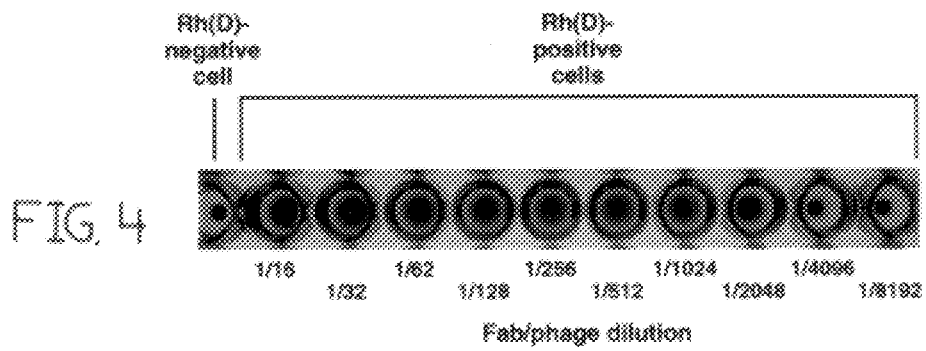
FIG. 4 is an image of a microplate agglutination assay wherein anti-Rh(D) Fab/phage agglutination titer was measured.

An RBC agglutination assay utilizing anti-M13 secondary antibody as bridging antibody was used to detect anti-Rh(D) Fab/phage activity in the panned polyclonal libraries and the individual randomly-picked Fab/phage clones (FIG. 4). The results shown are a representative example of the assay depicting negative reactivity to Rh(D)-negative RBCs and strongly positive reactivity to Rh(D)-positive RBCs for the $_{γ1}κ$ library (panning #2) out to a dilution of 1/2048.

In the case of the $_{γ1}κ$ library, significant enrichment for binding phage appears to occur after only one round of panning, whereas significant enrichment for the $_{γ1}λ$ library occurs during the second round. This is reflected by both the sharp increase in the percent of phage bound during a given round of panning as well as the ability of the polyclonal $_{γ1}κ$ and $_{γ1}λ$ Fab/phage libraries to agglutinate Rh(D)-positive RBCs after 1 and 2 rounds of panning, respectively (Table 1, FIG. 4).

Monoclonal Fab/phage were prepared from randomly-picked individual bacterial colonies obtained during each round of panning. It was apparent that by the third round of panning, all clones have anti-Rh(D) specificity (Table 1). To confirm that these Fab/phage have anti-Rh(D) specificity and are not binding to other unrelated antigens that may coincidentally be present on the particular Rh(D)-positive RBC and absent on the particular Rh(D)-negative RBC used in the agglutination assays, clones were screened against a panel of 11 Rh(D)-negative and-positive RBCs of varying blood group specificities to verify their anti-Rh(D) specificity (Walker, 1993, supra).

Clonal Analysis at the Genetic Level

To investigate the genetic diversity among the randomly picked anti-Rh(D) clones, plasmid DNA was prepared from each of the clones and the corresponding heavy and light chain Ig nucleotide sequences were identified. In Table 2 there is listed a number of attributes for each clone including the name of the most closely-related germline heavy or light chain Ig gene. More detailed analysis at the nucleotide level revealed that among all of the anti-Rh(D) binding clones, there were a large number of unique heavy and light chain DNA sequences (Table 3). Because of the random shuffling of heavy and light chain gene segments which occurs during the creation of a Fab/phage display library (Barbas et al., 1991, supra), it is evident that these heavy chains and light chains combined to form nearly 50 different anti-Rh(D) antibodies.

A detailed multiple alignment analysis of the predicted amino acid sequences revealed a total of twenty-five unique heavy chain, eighteen unique kappa light chain and twenty-three unique lambda light chain proteins. Due to the combinatorial effect during library construction, these heavy and light chain gene segments paired to produce fifty unique Fab antibodies ($20_{\gamma1\kappa}$ and $30_{\gamma1\lambda}$). Of interest, all twenty five unique heavy chains and nearly all of the eighteen unique kappa light chains were derived from only 5 $V_H$III or four V$\kappa$I germline genes, respectively, while the lambda light chains were derived from a more diverse set of germline genes. Analysis of heavy and light chain nucleotide sequences from over sixty negative clones from the unpanned libraries were performed to verify the heterogeneity in variable region family representation before selection. Clones representing $V_H$ families I (13%), III (36%), IV (31%), V(15%) and VI (5%); V$\kappa$ families I (43%), II(14%), III (29%) and IV (14%); and V$\gamma$ families I (48%), II (4%), III (9%), IV (4%), V (9%), VI (17%) and VII (9%) were present.

Clonal Analysis at the Protein Level

Figure 5:
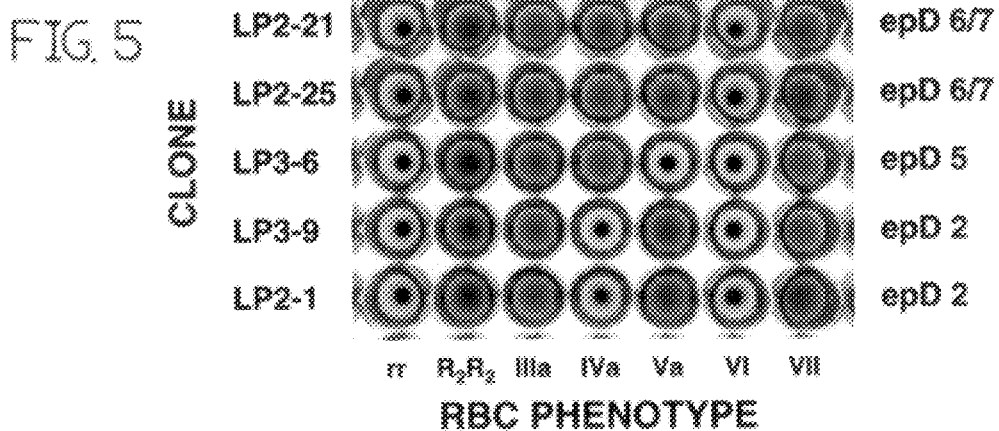
FIG. 5 is an image of a microplate agglutination assay showing determination of Rh(D) binding epitope for selected anti-Rh(D) Fab/phage clones.

To investigate the diversity in fine specificity (Rh(D) antigen epitope specificity) among the anti-Rh(D) clones, agglutination experiments were performed with selected clones and with sets of rare Rh(D)-positive RBCs which were obtained from individuals whose RBCs produce Rh(D) antigen lacking certain epitopes. Examining the pattern of agglutination of a particular anti-Rh(D) antibody with such sets of mutant RBCs enables the identification of the specific epitope on Rh(D) to which the antibody is directed (Mollison et al., 1993, supra). A representative example of such an experiment is shown in FIG. 5 and the Rh(D) epitopes for selected anti-Rh(D) Fab/phage clones are tabulated in Table 2.

Agglutination experiments were performed with anti-Rh (D)-negative RBCs (rr), Rh(D)-positive RBCs ($R_2R_2$), and "partial" Rh(D)-positive RBCs (mosaics IIIa, IVa, Va, VI, VII). The results shown are a representative example of the assay for 5 randomly-picked anti-Rh(D) Fab/phage clones (FIG. 5).

TABLE 1a.

$_{\gamma1}\kappa$FAB/PHAGE LIBRARY PANNING RESULTS

| PANNING[1] | φINPUT (CFUs)[2] | φOUTPUT (CFUs)[3] | % BOUND[4] ($\times 10^{-4}$) | ENRICHMENT[5] | AGGLUT- TITER[6] | BINDERS/ TOTAL(%)[7] |
|---|---|---|---|---|---|---|
| 0 | | | | | 0 | 0/16(0) |
| 1 | $2.94 \times 10^{11}$ | $6.04 \times 10^5$ | 2.1 | | 1/16 | 0/16 (0) |
| 2 | $2.15 \times 10^{11}$ | $1.68 \times 10^7$ | 78.3 | 38.0x | 1/2048 | 15/15 (100) |
| 3 | $1.72 \times 10^{11}$ | $1.44 \times 10^8$ | 840.0 | 10.7x | 1/2048 | 12/12 (100) |

TABLE 1b.

$_{\gamma1}\lambda$FAB/PHAGE LIBRARY PANNING RESULTS

| PANNING[1] | φINPUT (CFUs)[2] | φOUTPUT (CFUs)[3] | % BOUND[4] ($\times 10^{-4}$) | ENRICHMENT[5] | AGGLUT- TITER[6] | BINDERS/ TOTAL(%)[7] |
|---|---|---|---|---|---|---|
| 0 | | | | | 0 | 0/16(0) |
| 1 | $2.28 \times 10^{11}$ | $3.48 \times 10^5$ | 1.5 | | 0 | |
| 2 | $5.51 \times 10^{11}$ | $1.34 \times 10^6$ | 2.4 | 1.6x | 1/128 | 32/36 (89) |
| 3 | $3.93 \times 10^{11}$ | $3.86 \times 10^8$ | 980.0 | 404.0x | 1/512 | 24/24(100) |
| 4 | $2.87 \times 10^{11}$ | $3.08 \times 10^8$ | 1100.0 | 1.1x | 1/1024 | |

[1]panning round, where "0" represents the initial, unpanned Fab/phage library
[2]number of colony-forming units (CFUs) of phage (φ) incubated with Rh(D)-positive/-negative RBC admixture
[3]total number of CFUs of φ contained in eluate
[4](φoutput/φinput) × 100
[5]fold increase in % bound from compared to previous round of panning
[6]agglutination titer; see text and FIG. 4number of Rh(D)-binding Fab/phage clones per total number of clones screened from panning round; see Table 2 for details TABLE 2a.

ANALYSIS OF $_{\gamma 1}\kappa$FAB/PHAGE CLONES

| CLONE[1] | AGGLU[2] | VH FAM[3] | VH GENE[4] | Vκ FAM[5] | Vκ GENE[6] | D EPITOPE[7] |
|---|---|---|---|---|---|---|
| KPO-1 | neg | 3 | DP-47/V3-23 | 4 | DPK24/VklVKlobeck | |
| KPO-2 | neg | 3 | DP-31/V3-9P | 3 | DPK22/A27 | |
| KPO-3 | neg | 3 | DP-58/hv3dlEG | 4 | DPK24/VklVKlobeck | |
| KPO-4 | neg | 4 | 3d279d+ | — | no light chain | |
| KPO-5 | neg | 3 | DP-29/12-2 | 1 | LFVK431 | |
| KPO-6 | neg | 4 | DP-79/4d154 | 1 | DPK9/012 | |
| KPO-7 | neg | 3 | V3-48/hv3dl | 4 | DPK24/VklVKlobeck | |
| KPO-8 | neg | 4 | DP-70/4d68 | 2 | DPK18/A17 | |
| KPO-9 | neg | 1 | DP-14/Vl-18 | 1 | DPK9/012 | |
| KPO-10 | neg | 4 | DP-70/4d68 | 1 | DPK9/012 | |
| KPO-11 | neg | 5 | DP-73/V5-51 | 1 | DPK9/012 | |
| KPO-12 | neg | 3 | DP-54/V3-7 | 2 | DPK18/A17 | |
| KPO-13 | neg | 3 | V3-48/hv3dl | 1 | Vb' | |
| KPO-14 | neg | 6 | DP-74/VR-VI | 1 | DPK6JVb" | |
| KPO-15 | neg | 3 | DP-46/3d216 | 3 | Vg/38K | |
| KPO-16 | neg | 6 | DP-74/VH-VI | 1 | DPK9/012 | |
| KPI-1 | neg | 4 | V71-4+ | 3 | DPK22/A27 | |
| KPI-2 | neg | 4 | 3d279d+ | 1 | DPK8JVd+ | |
| KPI-3 | neg | 1 | 4M28 | 1 | DPK9/012 | |
| KPI-4 | neg | 4 | DP-79/4d154 | 3 | Vg/38K | |
| KPI-5 | neg | 3 | DP-38/9-1 | 3 | DPK22/A27 | |
| KPI-6 | neg | 4 | DP-70/4d68 | 1 | L12a/PCRdil6-5 | |
| KPI-7 | neg | 5 | DP-73/V5-51 | 2 | DPK15/A19 | |
| KPI-8 | neg | 4 | DP-7014d68 | 3 | DP22/A27 | |
| KPI-9 | neg | — | no heavy chain | — | no light chain | |
| KPI-10 | neg | — | no heavy chain | 3 | DPK22/A27 | |
| KPI-11 | neg | 1 | DP-15/V1-8+ | 1 | DPK9/012 | |
| KPI-12 | neg | 3 | b28e | — | no light chain | |
| KPI-13 | neg | 3 | DP-47/V3-23 | 4 | DPK24/VklVKlobeck | |
| KPI-14 | neg | 3 | DP-31/V3-9P | 3 | DPK21/humkv328h5 | |
| KPI-15 | neg | 1 | DP-7/21-2 | 4 | DPK24/VklVKlobeck | |
| KPI-16 | neg | 5 | DP-73N51 | 3 | DPK22/A27 | |
| KP2-1 | pos | 3 | DP-50/hv3019b9 | 1 | DPK9/012 | epD6/7 |
| KP2-2 | pos | 3 | DP-50/hv3019b9 | 1 | DPK9/012 | epD6/7 |
| KP2-3 | pos | 3 | DP-50/hv3019b9 | 1 | DPK9/012 | epD6/7 |
| KP2-4 | pos | 3 | b28m | 1 | DPK9/012 | epD2 |
| KP2-5 | pos | 3 | b28m | 1 | DPK9/012 | epD1 |
| KP2-6 | pos | 3 | DP-50/hv3019b9 | 1 | DPK9/012 | epD6/7 |
| KP2-7 | pos | 3 | DP-50/hv3019b9 | 1 | DPK9/012 | epD5 |
| KP2-8 | pos | 3 | DP-50/hv3019b9 | 1 | DPK9/012 | |
| KP2-9 | pos | 3 | DP-50/hv3019b9 | 1 | DPK9/012 | epD2 |
| KP2-10 | pos | 3 | DP-50/hv3019b9 | 1 | DPK9/012 | epD2 |
| KP2-11 | pos | 3 | DP-50/hv3019b9 | 1 | DPK9/012 | epD2 |
| KP2-12 | pos | 3 | DP-50/hv3019b9 | 1 | DPK9/012 | epD1 |
| KP2-13 | pos | 3 | DP-50/hv3019b9 | 1 | DPK9/012 | epD6/7 |
| KP2-14 | pos | 3 | DP-50/hv3019b9 | 2 | DPK15/A19 | epD2 |
| KP2-15 | pos | 3 | DP-50/hv3019b9 | 1 | DPK9/012 | epD6/7 |
| KP3-1 | pos | 3 | DP-50/hv3019b9 | 1 | DPK9/012 | |
| KP3-2 | pos | 3 | DP-50/hv3019b9 | 1 | DPK9/012 | epD6/7 |
| KP3-3 | pos | 3 | DP-50/hv3019b9 | 1 | DPK9/012 | |
| KP3-4 | pos | 3 | DP-49/1.9111 | 1 | DPK9/012 | epD5 |
| KP3-5 | pos | 3 | DP-50/hv3019b9 | 1 | DPK9/012 | |
| KP3-6 | pos | 3 | DP-50/hv3019b9 | 1 | A30/SG3+ | epD6/7 |
| KP3-7 | pos | 3 | DP-50/hv3019b9 | 1 | DPK8/Vd+ | epD6/7 |
| KP3-8 | pos | 3 | DP-50/hv3019b9 | 1 | DPK9/012 | epD6/7 |
| KP3-9 | pos | 3 | DP-50/hv3019b9 | 1 | DPK9/012 | |
| KP3-10 | pos | 3 | DP-50/hv3019b9 | I | DPK9/012 | |
| KP3-11 | pos | 3 | DP-50/hv3019b9 | 1 | DPK9/012 | |
| KP3-12 | pos | 3 | DP-46/3d216 | 1 | DPK9/012 | |

[1]nomenclature: prefix "LPO" denotes "$_{\gamma 1}\lambda$Fab/phage library, panning 0", "LP1" denotes "$_{\gamma 1}\lambda$Fab/phage library, panning 1", etc.
[2]agglutination negative or positive against Rh(D)-positive RBC
[3]Ig heavy chain variable region gene family per Tomlinson et al., supra
[4]closest related Ig heavy chain variable region gene per Tomlinson et al., supra
[5]Ig light chain variabie region gene famiiy per Tomlinson et al., supra
[6]closest related Ig light chain variable region gene per Tomlinson et al., supra
[7]Rh(D) epitope as defined by rare RBC agglutination pattern (see FIG. 5 and text)

TABLE 2b.

ANALYSIS OF γ1λFAB/PHAGE CLONES

| CLONE[1] | AGGLU[2] | VH FAM[3] | VH GENE[4] | Vκ FAM[5] | Vκ GENE[6] | D EPITOPE[7] |
|---|---|---|---|---|---|---|
| LPO-1 | neg | 4 | DP-65/3d75d | 1 | DPL7/IGLV1S2 | |
| LPO-4 | neg | 4 | DP-70/4d68 | 6 | IGLV8A1 | |
| LPO-3 | neg | 6 | DP-74/VH-V1 | 7 | DPL18/VL7.I | |
| LPO-4 | neg | 3 | DP-29/12-2 | 1 | DPL3/Iv122 | |
| LPO-5 | neg | 3 | DP-38/9-1 | 6 | IGLV6S1/LV6SW-G | |
| LPO-6 | neg | 1 | 4M28 | 1 | DPL3/Iv122 | |
| LPO-7 | neg | 1 | 8M27 | 1 | DPL2/Iv1L1 | |
| LPO-8 | neg | 5 | DP-58/V5-51 | 6 | IGLV6S1/LV6SW-G | |
| LPO-9 | neg | 5 | DP-73/V5-51 | 1 | DPL7/IGLV1S2 | |
| LPO-10 | neg | 3 | DP-38/9-1 | 1 | DPL2/IvlLl | |
| LPO-11 | neg | 3 | DP-3/V3-9P | 3 | DPL23/VLIII.1 | |
| LPO-12 | neg | — | no heavy chain | 1 | DPL7/IGLVlS2 | |
| LPO-13 | neg | 3 | DP-47/V3-23 | — | no light chain | |
| LPO-14 | neg | 4 | DP-71/3d197d | 6 | IGLV6S1/LV6SW-G | |
| LPO-15 | neg | 4 | DP-70/4d68 | 4 | IGLV8A1 | |
| LPO-16 | neg | 3 | DP-54/V3-7 | 7 | DPL19 | |
| LP2-1 | pos | 3 | DP-50/hv3019b9 | 1 | DPL2/Iv1L1 | epD2 |
| LP2-2 | pos | 3 | DP-77/WHG16 | 1 | DPL3/Iv122 | |
| LP2-3 | pos | 3 | DP-49/1.9111 | 1 | DPL3/Iv122 | epD1 |
| LP2-4 | neg | 4 | 3d279d+ | 1 | DPL2/Iv1L1 | |
| LP2-5 | pos | 3 | DP-49/1.9111 | 3 | DPL16/IGLV3S1 | epD5 |
| LP2-6 | pos | 3 | DP-50/hv3019b9 | 1 | DPL7/IGLV1S2 | epd2 |
| LP2-7 | pos | 3 | b28m | 1 | DPL7/IGLV1S2 | epD2 |
| LP2-8 | pos | 3 | DP-49/1.9111 | 3 | IGLV3S2=1v318 | epD1 |
| LP2-9 | pos | 3 | DP-50/hv3019b9 | 3 | DPL16/IGLV3S1 | epD2 |
| LP2-10 | pos | 3 | DP-77/WHG16 | 1 | DPL3/LV122 | |
| LP2-11 | neg | 1 | DP-75-VI-2 | 1 | DPL5/LV117d | |
| LP2-12 | pos | 3 | DP-77/WHG16 | 1 | DPL2/LV1L1 | epD2 |
| LP2-13 | pos | 3 | COS-8/hv3005f3 | 4 | IGLV8A1 | |
| LP2-14 | pos | 3 | DP-49/1.9111 | 1 | DPL7/IGLV1S2 | epD5 |
| LP2-15 | pos | 3 | DP-50/hv3019b9 | 3 | DPL16/IGLV3S1 | |
| LP2-16 | pos | 3 | DP-49/1.9111 | 2 | 1v2046 | epd1 |
| LP2-17 | pos | 3 | DP-77/WHG16=V3-21+ | 1 | DPL3/Iv122 | epD3/9 |
| LP2-18 | pos | 3 | DP-49/1.9111 | 2 | VL2.1~DPL10/Iv2O66 | epD1 |
| LP2-19 | pos | 3 | DP-50/hv3019b9 | 3 | DPL161IGLV3SI | epD2 |
| LP2-20 | neg | 3 | V3-49+ | 3 | DPLI6/IGLV3S1 | |
| LP2-21 | pos | 3 | DP-50/hv3019b9 | 7 | DPLI8/VL7.1 | epD6/7 |
| LP2-22 | pos | 3 | DP-49/1.9111 | 2 | Iv2046 | |
| LP2-23 | pos | 3 | DP-49/1.9111 | 3 | DPL16/IGLV3S1 | epD5 |
| LP2-24 | pos | 3 | DP-77/WHG16 | 1 | DPL3/Iv122 | |
| LP2-25 | pos | 3 | DP-50/hv3019b9 | 7 | DPL18/VL7.1 | epD6/7 |
| LP2-26 | pos | 3 | DP-49/1.9111 | 3 | DPL16/IGLV3S1 | |
| LP2-27 | neg | 3 | COS-6/DA-8 | 2 | VL2.1 | |
| LP2-28 | pos | 3 | COS-8/hv3005f3 | 4 | IGLV8A1 | |
| LP2-29 | pos | 3 | DP-49/1.9111 | | DPL13 | |
| LP2-30 | pos | 3 | DP-50/hv3019b9 | 3 | DPL16/IGLV3S1 | |
| LP2-31 | pos | 3 | DP-50/hv3019b9 | 7 | DPL18/VL7.1 | |
| LP2-32 | pos | 3 | DP-49/1.9111 | 1 | DPL2/Iv1L1 | |
| LP2-33 | pos | 3 | DP-50/hv3019b9 | 7 | DPL18/VL7.1 | |
| LP2-34 | pos | 3 | DP-50/hv3019b9 | 7 | DPL18/VL7.1 | |
| LP2-35 | pos | 3 | DP-50/hv3019b9 | 3 | DPL16/IGLV3S1 | |
| LP2-36 | pos | 3 | DP-50/hv3019b9 | 3 | DPL16/IGLV3S1 | |
| LP3-1 | pos | 3 | DP-50/hv3019b9 | 3 | DPL16/IGLV3S1 | epD2 |
| LP3-2 | pos | 3 | DP-49/1.9111 | 3 | DPL16/IGLV3S1 | epD1 |
| LP3-3 | pos | 3 | DP-49/1.9111 | 3 | DPL16/IGLV3S1 | |
| LP3-4 | pos | 3 | DP-50/hv3019b9 | 7 | DPL18/VL7.I | epD6/7 |
| LP3-5 | pos | 3 | DP-49/1.9111 | 1 | DPL5/LVll7d | epD5 |
| LP3-6 | pos | 3 | DP-49/1.9111 | 1 | DPL5/LVll7d | epD1 |
| LP3-7 | pos | 3 | DP-77/WHG16 | 1 | DPL2/Iv1L1 | epD5 |
| LP3-8 | pos | 3 | b28m | I | DPL7/IGLVIS2 | epD2 |
| LP3-9 | pos | 3 | DP-50/hv3019b9 | 3 | DPL16/IGLV3S1 | epD2 |
| LP3-10 | pos | 3 | DP-50/hv3019b9 | 3 | DPL16/IGLV3S1 | |
| LP3-11 | pos | 3 | DP-50/hv3019b9 | 3 | DPL16/IGLV3S1 | epD2 |
| LP3-12 | pos | 3 | COS-8/hv3005f3 | 4 | 1GLV8A1 | epD6/7 |
| LP3-13 | pos | 3 | DP-50/hv3019b9 | 1 | DPL2/IvlLl | epD2 |
| LP3-14 | pos | 3 | DP-49/1.9111 | 3 | DPL16/IGLV3S1 | |
| LP3-15 | pos | 3 | DP-77/WHG16 | 1 | DPL3/Iv122 | epD1 |
| LP3-16 | pos | 3 | DP-49/1.9111 | 1 | DPL2/IvIL1 | epD5 |
| LP3-17 | pos | 3 | DP-50/hv3019b9 | 3 | DPL16/IGLV3SI | |
| LP3-18 | pos | 3 | DP-50/hv3019b9 | 3 | DPL16/IGLV3S1 | |
| LP3-19 | pos | 3 | DP-50/hv3019b9 | 3 | DPL16/IGLV3S1 | epD5 |
| LP3-20 | pos | 3 | DP-50/hv3019b9 | 1 | DPL2/IvlLI | |
| LP3-21 | pos | 3 | DP-49/1.9111 | 1 | DPL3/1v122 | |

TABLE 2b.-continued

ANALYSIS OF $_{\gamma 1}\lambda$FAB/PHAGE CLONES

| CLONE[1] | AGGLU[2] | VH FAM[3] | VH GENE[4] | Vκ FAM[5] | Vκ GENE[6] | D EPITOPE[7] |
|---|---|---|---|---|---|---|
| LP3-22 | pos | 3 | COS-8/hv3005f3 | 1 | DPL2/Iv1L1 | |
| LP3-23 | pos | 3 | DP-49/1.9111 | 3 | DPL16/IGLV3S1 | |
| LP3-24 | pos | 3 | DP-50/hv3019b9 | 3 | DPL16/IGLV3S1 | |

[1]nomenclature: prefix "LPO" denotes "$_{\gamma 1}\lambda$Fab/phage library, panning 0", "LP1" denotes "$_{\gamma 1}\lambda$Fab/phage library, panning 1", etc.
[2]agglutination negative or positive against Rh(D)-positive RBC
[3]Ig heavy chain variable region gene family per Tomlinson et al., supra
[4]closest related Ig heavy chain variable region gene per Tomlinson et al., supra
[5]Ig light chain variabie region gene famiiy per Tomlinson et al., supra
[6]closest related Ig Iight chain variable region gene per Tomlinson et al., supra
[7]Rh(D) epitope as defined by rare RBC agglutination pattern (see FIG. 5 and text)

TABLE 3

SUMMARY OF FAB/PHAGE CLONAL ANALYSIS

| | |
|---|---|
| Number of unique heavy chains | 25 |
| Number of unique κ light chains | 18 |
| Number ofunique λ light chains | 23 |
| Number of $_{\gamma 1}$κ antibodies | 20 |
| Number of $_{\gamma 1}$λ antibodies | 30 |
| Number Rh(D) epitope specificities represented | 5 |

Use of Fab/Phage Antibodies as Blood Bank Typing Reagents

The ability of the anti-Rh(D) Fab/phage preparations to accurately distinguish Rh(D)-negative from Rh(D)-positive RBCs in microplate hemagglutination assays (FIGS. 4 and 5) provided evidence that a gel test (Lapierre et al., 1990, Transfusion 30:109–1130) used by blood banks to phenotype RBCs using conventional antisera could be adapted for use with Fab/phage.

Figure 6:
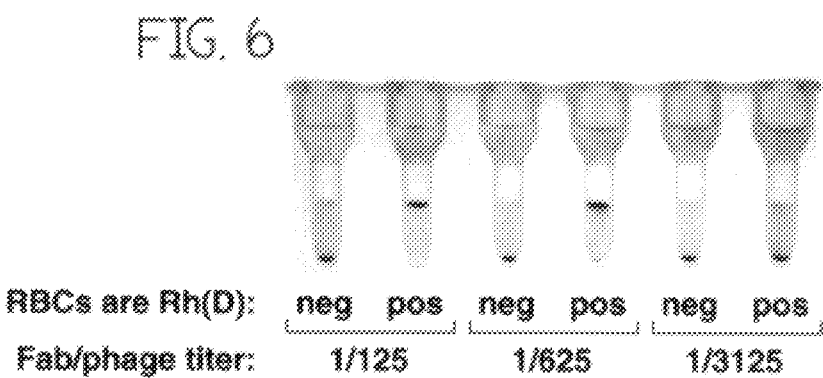
FIG. 6 is an image depicting the use of Fab/phage antibodies in a gel card assay.

The gel test comprises a plastic card of approximately 5×7 cm, containing 6 minicolumns each filed with about 20 μl of dextran-acrylamide beads suspended in anti-human globulin (Coombs reagent). Red cells to be typed are incubated with the desired human anti-sera and are centrifuged through the gel. RBCs which are positive for antigens to which the antisera is directed agglutinate as they encounter the anti-human globulin and become trapped in or above the gel matrix. Unreactive RBCs sediment through the gel particles and form a pellet at the bottom of the microtube. Because the gel test offers a number of advantages over traditional blood banking methods for RBC phenotyping including decreased reagent volumes, the elimination of a cell washing step and a more objective interpretation of results, many blood bank facilities have adapted this new technology. As shown in FIG. 6, anti-Rh-(D) Fab/phage can be used with gel cards that are modified to contain anti-M13 antibody.

To perform the assay, Rh(D)-negative or -positive red blood cells were incubated with dilutions of anti-Rh(D) Fab/phage ($_{\gamma 1}$κ library, panning #2) and were centrifuged into microcolumns containing beads suspended in anti-M1 3 antibody. Undiluted Fab/phage stock had a titer of 5×10$^{12}$ cfu/ml similar to that in the microplate settling assay (FIG. 4). Because the volume of Fab/phage used in this assay is one-fourth of that in the microplate assay, the amount of Fab/phage present in the 1/625 dilution is approximately equal to that present in the 1/2048 dilution in FIG. 4. Therefore, the number of Fab/phage required to yield a positive result is essentially equivalent in both assays.

In other assays which were performed as just described, when anti-M13 antibody was eliminated from the assay, no agglutination of red blood cells was observed. In addition, anti-IgG antibody does not react with recombinant Fabs expressed on the surface of the bacteriophage. Only Rh-positive cells which were reacted with anti-Rh phage were agglutinated when anti-M13 antibody was present in the assay. It should be noted that when high concentrations of anti-M13 antibody were used, even Rh-negative cells appeared to be agglutinated. This is an artifact resulting from the cross-linking of unbound (i.e., unreacted) phage which becomes crosslinked in the presence of high amounts of anti-M13 antibody and forms a semi-impenetrable mat through which not all the Rh-negative cells can traverse. In the experiments described herein, an anti-M 13 concentration of about 100 μg/ml was considered to be optimal for agglutination and for the prevention of false positive results. Depending on the precise concentrations of reagents and cells used in the assay, the concentration of anti-M13 may deviate from this number.

To assess the relative sensitivity of an anti-M13 modified Micro Typing System, the columns of the Micro Typing System cards had added to them 100 μg/ml of anti-M13 antibody. Rh-negative or Rh-positive red blood cells were incubated with undiluted or with five-fold serial dilutions (1/5, 1/25, 1/125, 1/625 and 1/3125) of anti-Rh phage antibodies. The cards were centrifuged and samples were assessed for agglutination. The modified Micro Typing System card assay was capable of detecting anti-Rh agglutination at a dilution of between 1/625 and 1/3125.

Procedures for Isolation of Tumor-Specific Antibodies

Fab/phage specific for tumor cells are useful for in vitro diagnosis (lab assays of biopsy, fluid, or blood samples), in vivo labeling of tumor/metastasis (coupling of antibody to imaging probe), or for treatment of malignancy (coupling of antibodies to chemical or radioactive toxins). Tumor-specific antibodies are also useful for the identification of novel antigens or markers on tumor cells which may form the basis for anti-tumor vaccines. Further, tumor-specific antibodies useful for the generation of anti-idiotypic antibodies may also form the basis for anti-tumor vaccines.

Anti-tumor antibodies are generated essentially as described herein for the generation of anti-Rh antibodies. Tumor cells, for example, but not limited to, malignant melanoma cells, are cell-surface biotinylated, labeled with streptavidin-magnetic microbeads, and are then mixed with excess normal melanocytes. Fab/phage libraries are generated from peripheral blood lymphocytes of melanoma patients who possess therapeutically useful anti-tumor antibodies. A number of melanoma patients who have "cured" themselves apparently have done so by mounting a humoral (i.e., antibody) immune response. These Fab/phage libraries are incubated with the admixture of cells. Fab/phage which are directed against epitopes specific for malignant cells will bind to the malignant cells and may then be isolated utilizing the magnetic column panning approach.

Isolation of Fab/Phage That Identify Bacterial Virulence Factors

The approach described herein may be used to isolate Fab/phage capable of detecting differences between the virulent bacteria and their nonpathogenic counterparts. In this case, the virulent strain of bacteria is magnetically labeled, diluted with the non-pathogenic counterpart, and an Fab/phage library which is generated from lymphocytes obtained from individuals infected with the virulent strain is added. Fab/phage which are isolated in this manner may be useful for the identification of novel bacterial antigens against which antibacterial compounds and/or vaccines may be developed.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of isolating a DNA encoding a protein which binds to an antigen-bearing moiety, said method comprising
    generating a phage display library comprising a plurality of virus vectors, wherein at least one of said virus vectors expresses said protein on the surface thereof and comprises said DNA, said DNA being heterologous with respect to said virus vector;
    adding a magnetic label to cells bearing said antigen-bearing moiety on their surface, thereby producing magnetically labeled cells;
    incubating said phage display library with said magnetically labeled cells in the presence of an excess of unlabeled cells which do not express said antigen-bearing moiety to form a mixture, whereby said at least one virus vector binds to said magnetically labeled cells;
    isolating magnetically labeled cells from said mixture, whereby said at least one virus vector is isolated from said mixture, and
    obtaining DNA encoding said protein from said isolated virus vector.

2. The method of claim 1, wherein said phage display library is a synthetic phage display library.

3. The method of claim 1, wherein said magnetically labeled cells are isolated from said mixture by applying said mixture to a magnetic separation column and eluting said unlabeled cells from said column.

4. A method of isolating a protein which binds to an antigen-bearing moiety, said method comprising generating a phage display library comprising a plurality of virus vectors, wherein at least one of said virus vectors comprises a heterologous DNA encoding said protein and expresses said protein on the surface thereof;
    adding a magnetic label to cells bearing said antigen-bearing moiety on their surface, thereby producing magnetically labeled cells;
    incubating said phage display library with said magnetically labeled cells in the presence of an excess of unlabeled cells which do not express said antigen-bearing moiety to form a mixture, whereby said at least one virus vector binds to said magnetically labeled cells;
    isolating magnetically labeled cells from said mixture, whereby said at least one virus vector is isolated from said mixture, and
    isolating said protein from said isolated virus vector.

5. The method of claim 4, wherein said DNA library is a synthetic phage display library.

6. The method of claim 4, wherein said magnetically labeled cells are isolated from said mixture by applying said mixture to a magnetic separation column and eluting said unlabeled cells from said column.

7. The method of claim 3, wherein said mixture is applied to said column in the absence of a magnetic field.

8. The method of claim 1 or 4, wherein said virus vector is selected from the group consisting of a bacteriophage M13 vector and a bacteriophage lambda vector.

9. The method of claim 1 or 4, wherein said protein is selected from the group consisting of an antibody, a ligand and a hormone.

10. The method of claim 1 or 4, wherein said protein is an antibody.

11. The method of claim 6, wherein said mixture is applied to said column in the absence of a magnetic field.

12. The method of claim 8, wherein said virus vector is a bacteriophage M13 vector.

13. The method of claim 9, wherein said protein is an antibody.

14. The method of claim 10, wherein said antigen-bearing moiety is a membrane bound protein.

15. The method of claim 13, wherein said antibody is an anti-red blood cell surface antigen antibody.

16. The method of claim 14, wherein said membrane bound protein is selected from the group consisting of an antigen and a receptor protein.

17. The method of claim 15, wherein said antibody is an anti-Rh red blood cell antibody.

18. The method of claim 15, wherein said antibody is an anti-Rh(D) red blood cell antibody.

19. The method of claim 16, wherein said membrane bound protein is an antigen.

20. The method of claim 19, wherein said antigen is a red blood cell antigen.

21. The method of claim 20, wherein said antigen is a Rh antigen.

22. A method of isolating a DNA encoding a protein which binds to a cell receptor, said method comprising
    generating a phage display library comprising a plurality of virus vectors, wherein at least one of said virus vectors expresses said protein on the surface thereof and comprises said DNA, said DNA being heterologous with respect to said virus vector;
    adding a magnetic label to cells bearing said cell receptor on their surface, thereby producing magnetically labeled cells;
    incubating said phage display library with said magnetically labeled cells in the presence of an excess of unlabeled cells which do not express said cell receptor to form a mixture, whereby said at least one virus vector binds to said magnetically labeled cells;

isolating magnetically labeled cells from said mixture, whereby said at least one vector is isolated from said mixture; and obtaining DNA encoding said protein from said isolated virus vector.

23. A method of isolating a protein which binds to a cell receptor, said method comprising generating a phage display library comprising a plurality of virus vectors, wherein at least one of said virus vectors comprises a heterologous DNA encoding said protein and expresses said protein on the surface thereof;

adding a magnetic label to cells bearing said cell receptor on their surface, thereby producing magnetically labeled cells;

incubating said phage display library with said magnetically labeled cells in the presence of an excess of unlabeled cells which do not express said cell receptor to form a mixture, whereby said at least one virus vector binds to said magnetically labeled cells;

isolating magnetically labeled cells from said mixture, whereby said at least one vector is isolated from said mixture; and isolating said protein from said isolated virus vector.

24. The method of claim 22 or 23, wherein said protein is selected from the group consisting of a ligand and a hormone.

* * * * *